United States Patent [19]

Edgington et al.

[11] 4,140,753

[45] Feb. 20, 1979

[54] DIAGNOSTIC METHOD AND REAGENT

[75] Inventors: Thomas S. Edgington, La Jolla; Edward F. Plow, San Diego, both of Calif.

[73] Assignee: Scripps Clinic & Research Foundation, La Jolla, Calif.

[21] Appl. No.: 682,028

[22] Filed: Apr. 30, 1976

[51] Int. Cl.² .............................................. A61K 43/00
[52] U.S. Cl. ...................................... 424/1; 23/230 B; 260/112 R; 424/12; 424/88
[58] Field of Search .................. 23/230 B; 260/112 R; 424/1

[56] References Cited

U.S. PATENT DOCUMENTS

| 3,663,684 | 5/1972 | Freedman et al. | 424/1 |
| 3,697,638 | 10/1972 | Hansen | 424/1 |
| 3,823,126 | 7/1974 | Bjorklund | 260/112 R |
| 3,867,363 | 2/1975 | Hansen | 260/112 R |
| 3,956,258 | 5/1976 | Hansen | 260/112 R |
| 3,960,827 | 6/1976 | Bjorklund | 260/112 R |

Primary Examiner—Leland A. Sebastian
Attorney, Agent, or Firm—Knobbe, Martens, Olson, Hubbard & Bear

[57] ABSTRACT

The discovery of an isomeric species of carcinoembryonic antigen and methods of isolation, identification and utilization as a radiolabelled species of the same as an aid in the diagnosis of adenocarcinomas of the gastrointestinal tract are disclosed.

13 Claims, No Drawings

DIAGNOSTIC METHOD AND REAGENT

The invention described herein was made in the course of work under a grant or award from the Department of Health, Education and Welfare.

RELATED APPLICATION

Application Ser. No. 682,027 filed concurrently herewith on Apr. 30, 1976, CARCINOEMBRYONIC ANTIGEN ISOMER, Thomas S. Edgington and Edward F. Plow.

INCORPORATION BY REFERENCE

The aforesaid patent application Ser. No. 682,027, filed concurrently herewith on Apr. 30, 1976, and the publications of the inventors, ISOLATION AND CHARACTERIZATION OF A HOMOGENEOUS SPECIES OF CARCINOEMBRYONIC ANTIGEN: CEA-S, Int. J. Cancer: 15, 748–761, 1975, and ASSOCIATION OF AN ISOMERIC SPECIES OF CARCINOEMBRYONIC ANTIGEN WITH NEOPLASIA OF THE GASTROINTESTINAL TRACT, (with Robert W. Astarita), New Eng. J. of Med., 293:103–107 (July 17) 1975, are incorporated herein by reference as fully as though reproduced as part of this specification.

FIELD OF THE INVENTION

This invention relates to a radioimmunoassay of improved specificity for the diagnosis of cancer of the gastrointestinal tract of man.

BACKGROUND OF THE INVENTION

Carcinoembryonic antigen (CEA) has been defined as glycoprotein present during fetal and embryonic development of the human, present at very low concentration in the mucosal epithelium of the adult human gastrointestinal tract, and produced in high concentration by a variety of tumors of the gastrointestinal tract (Gold, P. & Freedman, S. O.: J. Exp. Med. 122: 439–462, 467–481, 1965).

CEA has been isolated from gastrointestinal tumors and characterized as an approximately 200,000 molecular weight glycoprotein by Gold and Freedman (J. Exp. Med. 128: 387–398, 1968) and by Coligan, J. E., et al (Immunochem. 10: 591–599, 1973).

CEA has been utilized in radioimmunoassays of serums for the detection of cancer in humans, first by Thompson, et al. (Proc. Natl. Acad. Sci. 64: 161–167, 1969) and subsequently by Lo Gerfo, et al. (New Engl. J. Med. 285: 138–141, 1971), Hansen, H. J., U.S. Pat. Nos. 3,697,638 (Oct. 10, 1972) and 3,867,363 (Feb. 18, 1975), Freedman, S. O., Gold, P., and Krupey, J. H., U.S. Pat. No. 3,663,684 (May 16, 1972) and others. This has not provided an adequately precise or specific test for the clinical diagnosis and management of cancer to date since a high incidence of false positive results (3–19% of normal controls and as high as 67% of patients with inflammatory bowel disease) are observed (Hansen, H. J.: Human Pathology 5: 139–147, 1974).

We have isolated what appears to be a tumor-dominant isomer, subspecies or variant of CEA (CEA-S$_1$). CEA-S is a glycoprotein of approximately 181,000, is devoid of blood group antigens, shares antigenic determinants with CEA but is also immunochemically distinguishable from CEA.

BRIEF SUMMARY

We have developed and proved the application of CEA-S$_1$ to an immunodiagnostic assay for the detection of tumors of the gastrointestinal tract (Edgington, T. S., Astarita, R. W. and Plow, E. F.: New Engl. J. Med. 293: 103–107, 1975). The use of this defined isomeric species of carcinoembryonic antigen, isolated from adenocarcinomas of the colon, in a radioimmunoassay of body fluids (i.e., serum) has provided a laboratory assay to distinguish between normal individuals and most of those with tumors of the gastrointestinal tract. The CEA-S$_1$ assay has been used to evaluate clinical application to the detection and management of human cancer of the gastrointestinal tract. 80.4% of patients with neoplasia of the gastrointestinal tract were positive whereas only 9.3% of other tumors, predominantly of lung and breast origin, were detectable. Serum levels were elevated in only 0.23% of random patients and 0.41% of 725 patients without neoplasia but including those with diseases frequently associated with false positive results by other CEA assays. The results of these studies suggest that CEA-S$_1$ may represent a tumor dominant isomeric species of carcinoembryonic antigen. Assays by this technique offer a new and an improved approach for diagnosis and management of cancer of the gastrointestinal tract.

GENERAL DESCRIPTION

1. Isolation of CEA-S$_1$. (Plow, E. F. and Edgington, T. S.: Int. J. Cancer 15: 748–761, 1975, and unpublished studies) CEA-S$_1$ is isolated from human adenocarcinomas of the gastrointestinal tract. Isolation involves (a) extraction of glycoprotein; (b) isolation of glycoproteins with a pI of approximately 4.4–4.6; (c) isolation of glycoproteins of approximately 200,000 by molecular exclusion chromatography; (d) recovery by ion exchange chromatography; (e) removal of other proteins, glycoproteins, and blood group antigen related molecules with immunoabsorbants; and (f) isolation of glycoprotein with a buoyant density of approximately 1.41.

This isolation involves: (1) tumor tissue is homogenized in approximately 1.5 volumes cold H$_2$O or saline screened through gauze and #25 mesh screening with washes of cold H$_2$O. The tumor homogenate is suspended at approximately three times the volume of the starting tumor weight at 4° C. and clarified by ultracentrifugation. The supernatant is brought at 0° C. to 0.9 M with perchloric acid (PCA). The supernatant is recovered following centrifugation and immediately brought to neutrality and dialyzed exhaustively. (2) The PCA soluble glycoprotein fraction is brought to 1% ampholyte concentration, pH 3–6. Precipitate is removed by centrifugation. An additional 1% ampholyte is added, and the sample is electrofocused. The major CEA antigen-containing peak of pI 4.4–4.6 is recovered. (3) This fraction is concentrated and separated by one or more molecular exclusion chromatography steps, typically utilizing first A-1.5 fine agarose (Biorad) then Sephadex G-200 and the peak of approximately 200,000 molecular weight with a Kd of 0.17 (G-200) is collected and retained as the CEA-S fraction. (4) This glycoprotein fraction is brought to 0.05 M Na$_2$HPO$_4$, pH 8.0, and passed through DEAE-cellulose column at 20–24° C. equilibrated with the same buffer to remove more highly charged species of glycoprotein. The first major peak is collected and retained. (5) The sample is then passed through immunoadsorbents containing antisera to blood group antigens, human serum proteins, human serum glycoproteins, and antisera to tissue glycoproteins other than CEA or CEA-$S_1$, i.e., NCA. (6) Following removal of these contaminants, the material that passes through this column is then subjected to equilibrium density gradient ultracentrifugation in cesium chloride. The CEA-$S_1$ (major band) with a density of approximately 1.41 gm/ml is recovered and utilized as CEA-$S_1$. The recovery of CEA-S varies between different tumors and represent 1-10% of the original tumor glycoprotein present in the PCA soluble tumor extract.

2. IDENTIFICATION AND CHARACTERIZATION OF CEA-$S_1$.

(a) Sedimentation velocity. CEA-$S_1$ has a $S°_{20,w}$ of 6.6 Svedberg units when analyzed by linear sucrose density gradient ultracentrifugation (Plow, E. F. & Edgington, T. S.: Int. J. Cancer 15: 748-761, 1975). This contrasts to a $S°_{20,w}$ of 6.8 for CEA when analyzed simultaneously.

(b) Immunochemical characteristics. CEA-$S_1$ precipitates with anti-CEA or anti-CEA-$S_1$ in gel double diffusion to give an arc of apparent identity with CEA (Plow, E. F. & Edgington, T. S.: Int. J. Cancer 15: 748-761, 1975). Utilizing a variety of equilibrium competitive inhibition radioimmunoassays for CEA-$S_1$ it is observed that preparation of CEA have 8-33% of the antigen activity of CEA-$S_1$ and show reactions of only partial quantitative identity with CEA-$S_1$. CEA-$S_1$ is preferentially bound by anti-CEA-$S_1$ antisera as compared to CEA. CEA-S is not bound by antiserum to blood group A or B antigens, Rh antigens, Kell, Duffy or Lewis a antigens, nor by antisera to normal tissue glycoprotein $NCA_1$ (von Kleist, S., Chavenel, G. & Burtin, P.: Proc. Natl. Acad. Sci. 69: 2492-2494, 1972). Some preparations of CEA are bound by antibodies to blood group A or B antigens and most are bound by antibodies to Lewis a. (Holburn, A. M., Mach, J. P., MacDonald, D. and Newlands, M., Immunology 26: 831-843, 1974.)

(c) Isoelectric point. CEA-$S_1$ has a single discrete isoelectric point of pI = 4.5 ± 0.1 using either isoelectric columns with ampholytes (LKB) with a pH range of 3-6 or thin layer pH 3-9 acrylamide gels containing ampholytes. By contrast, CEA has a variable distribution over a range of pH 3-5.2.

(d) Molecular exclusion chromatography. Characterization of CEA-$S_1$ by Sephadex G-200 gel exclusion chromatography gives values indistinguishable from CEA with: Kd = 0.17; $D°_{20,w}$ = 3.05 × $10^{-4}$ $cm^2$/sec; mean estimated stokes radius = 65 A (Plow, E. F. & Edgington, T. S.: Int. J. Cancer 15: 748-761, 1975 and unpublished data).

(e) Buoyant density. CEA-$S_1$ has a buoyant density, when isolate from typical colonic adenocarcinomas, of 1.41 ± 0.02 gm/ml determined by isopycnic equilibrium density gradient ultracentrifugation in cesium chloride. By contrast, CEA gives a major peak of approximately 1.36 gm/ml with a wide range of density distributions various subfractions (Plow, E. F. & Edgington, T. S.: Int. J. Cancer 15: 748-761, 1975, and unpublished data).

(f) Estimated molecular weight. Using the Svedberg equation and estimated molecular weight of 181,000 daltons has been determined for CEA-$S_1$ as contrasted to 201,000 daltons for CEA.

(g) Amino acid composition. The amino acid composition of the single polypeptide chain of CEA-$S_1$ is similar to CEA.

| Amino Acid Comparison of CEA and CEA-$S_1$/ Isolated from the Same Tumor | | | | |
|---|---|---|---|---|
| | $CEA_{0.1.3}$ | | $CEA-S_{1.1.3}$ | |
| Amino Acid | (M/$10^5$/$cm^*$) | (Rel. % of AA) | (M/$10^5$/$gm^*$) | (Rel. % of AA) |
| Lys | 27.0 | 3.0 | 30.0 | 3.3 |
| His | 16.4 | 1.8 | 15.9 | 1.8 |
| Arg | 32.0 | 3.5 | 33.3 | 3.6 |
| Asp | 131.1 | 14.4 | 127.6 | 14.0 |
| Thr | 80.5 | 8.8 | 76.2 | 8.4 |
| Ser | 92.9 | 10.2 | 90.4 | 9.9 |
| Glu | 98.8 | 10.8 | 97.6 | 10.7 |
| Pro | 67.9 | 7.4 | 69.3 | 7.6 |
| Gly | 58.2 | 6.4 | 56.2 | 6.2 |
| Ala | 53.3 | 5.8 | 52.7 | 5.8 |
| Val | 65.2 | 7.4 | 64.5 | 7.1 |
| Met | 1.9 | 0.2 | 1.9 | 0.2 |
| Ileu | 44.3 | 4.9 | 42.3 | 4.6 |
| Leu | 78.9 | 8.6 | 75.8 | 8.3 |
| Tyr | 32.9 | 3.6 | 31.2 | 3.4 |
| Phe | 23.3 | 2.6 | 21.6 | 2.4 |
| Trpy | 9.9 | 1.1 | 12.6 | 1.4 |
| Cys (½) | 12.2 | 1.3 | 14.5 | 1.6 |

*Based on 33.9% protein as determined from $E_{280}^{1\%}$ = 5.44 and amino acid yield on a Beckman 121 M amino acid analyser.

(h) Acrylamide gel electrophoresis in 1% sodium dodecyl sulfate at pH 7.0. (method of Weber, K. & Osborn, M.: J. Biol. Chem. 244: 4400-4412, 1969). CEA-$S_1$ gives a single discrete band with a relative mobility (Rm) of 0.143. It exhibits a slightly lower mobility and is considerably more discrete than CEA.

(i) Radioimmunoassay. CEA-$S_1$ has been used in radioimmunoassays for the detection, evaluation and management of cancer of the gastrointestinal tract (Edgington, T. S., Astarita, R. W., and Plow, E. F.: New. Engl. J. Med. 293: 103-107, 1975). Double blind clinical studies have been conducted to compare CEA-$S_1$ assays with CEA assays of the same sera. CEA-$S_1$ is also distinguishable from CEA by: (a) quantitative antigen binding assays with anti-CEA-$S_1$ and various anti-CEA sera and by (b) competitive inhibition assays using either $^{125}I$ CEA-$S_1$ or $^{125}I$ CEA as ligands and either anti-CEA-S or anti-CEA as antisera. In clinical studies CEA-$S_1$ assay of serum has given less than 1% false positive results (0.23 and 0.41%) as compared to 3-19% false positive for CEA assay (Hansen, H. J.: Human Pathology 5: 139-147, 1974). Detection of cancer of the gastrointestinal tract was 80.4% as compared to 72% with CEA assay and detection of non-gastrointestinal tumors has been very low as compared to equivalent detection by CEA assay.

3. CEA-$S_1$ radioimmunoassays.
RADIOIMMUNOASSAYS.

The CEA-$S_1$ assay employs three features:
(i) $^{125}I$ CEA-$S_1$ of colonic adenocarcinoma origin;
(ii) anti-CEA-S antiserum or selected anti-CEA antiserum exhibiting 2 to 3 fold preferential binding of $^{125}I$ CEA-$S_1$;
(iii) High ionic strength buffers such as 0.14 M NaCl, 0.10 M sodium borate buffer, pH 8.2.

ISOLATION AND CHARACTERIZATION OF of CEA-$S_1$

A single homogeneous isomeric species of carcinoembryonic antigen is isolated by reference to solubility in 0.9 M perchloric acid, isoelectric focusing, molecular exclusion chromatography, ion exchange chromatography, passage through immunoabsorbants, and isopyknic density gradient ultracentrifugation. The final product, representing approximately 1.8%-10% of the perchloric acid soluble glycoprotein of the tumor, is homogeneous and devoid of other proteins by polyacrylamide gel electrophoresis. This single species of carcinoembryonic antigen, CEA-S$_1$, has a sedimentation velocity of 6.6, a diffusion constant of $3.05 \times 10^{-7}$ cm$^2$/sec, a mean Stokes radius of 65 Å, a density of 1.41 ml/g in cesium chloride and an estimated molecular weight of 181,000, and it is devoid of detectable A, B, Rh, Kell, Duffy or Lewis a (Le-a) blood-group antigens. Immunochemical studies demonstrate qualitative similarities between CEA-S$_1$ and conventional carcinoembryonic antigens, however, competitive inhibition analyses demonstrate significant quantitative immunochemical differences between CEA-S$_1$ and preparations of carcinoembryonic antigen. These results are consistent with the concept that CEA-S$_1$ is an immunochemical isomer of carcinoembryonic antigen.

EXEMPLARY PROCEDURE

The following procedure is an example of the best mode of practicing the invention and does not limit the scope of the invention.

SOURCE AND EXTRACTION OF CEA-S

CEA-S is isolated from 300-600 g of tumor, representing hepatic metastases of primary adenocarcinomas of the colon. Normal tissue is removed by dissection and the tumor is minced, homogenized with approximately 1.5 vol cold H$_2$O or saline in a Polytron homogenizer, and passed through gauze or a 25-mesh screen with washes of cold H$_2$O or saline. The tumor is suspended in a total of 2 vol H$_2$O and stirred for 2-4 h at 4° C. The homogenate is clarified by ultracentrifugation at 22,000 $\times$ g for 16-18 h at 4° C. in a Spinco 15 rotor. The sediment is homogenized with 1 vol 1 M NaCl for 4-6 h at 4° C. and again clarified by ultracentrifugation. Supernatants from the first and second extractions are combined. An equal volume of cold 1.8 M perchloric acid (PCA) is slowly added dropwise to the tumor extract at 4° C., and after continuous stirring for 1 h the precipitate is removed by centrifugation at 1,800 $\times$ g for 1 h at 4° C. The supernatant containing the glycoprotein is brought to neutrality, then dialyzed exhaustively against distilled water, the final dialysis also containing mixed bed ion exchange resin (Biorad). (See Freedman, et al, U.S. Pat. No. 3,663,684). To facilitate detection of protein during subsequent isolation, the PCA-soluble glycoprotein fraction may be trace-labelled with $^{125}$I or may be followed by absorbance at 280 nm (E$_{280}$$^{1\%}$ = 5.44).

ISOELECTRIC FOCUSING

Isoelectric focusing of the PCA-soluble glycoprotein fraction is performed in a 440 ml LKB electrofocusing column using a 5 to 30% sucrose gradient containing 1% ampholytes, pH 3-6. Electrofocusing is conducted for 60 h at 3° C. maintaining maximum power of approximately 6 watts and increasing to a maximum potential difference at 700 V. The column is eluted and 5 ml fractions are collected.

ION EXCHANGE CHROMATOGRAPHY

Ion exchange chromatography is performed on a 2.5 $\times$ 30 cm column of DEAE-cellulose (Schleicher and Schuell, Inc., Keene, N. H., USA, 0.71 meq/g) at 20-24° C. equilibrated with 0.05 M Na$_2$HPO$_4$ starting buffer. The sample is applied following dialysis against the starting buffer, and a flow rate of 30 ml h is maintained until all of the initial non-bound fraction is eluted. The bond fraction is eluted with 0.50 M NaH$_2$PO$_4$.

MOLECULAR EXCLUSION CHROMATOGRAPHY

Preparative molecular exclusion chromatography is performed first on Biorad A 1.5 fine agarose and then on Sephadex G-200 (2.5 $\times$ 80 cm column) both equilibrated with 0.14 M NaCl, 0.01 M sodium phosphate, pH 6.0. A flow rate of 5-6 ml/cm$^2$ cross-sectional area/hr for A 1.5 and 3.5-4.0 ml/cm$^2$ cross sectional-area/h for Sephadex G-200 is used. The Kd of the Sephadex G-200 is calculated using a dextran blue determined Vo of 160 ml and a Na$^{51}$Cr determined Vi of 234 ml (Gelotte, 1960). The diffusion constant (D$_{20,w}$) and Stokes radius of CEA-S$_1$ are estimated graphically from the Kd, utilizing proteins with known physical constants for calibration (Siegel and Monty, 1966). Standards included human figrinogen, catalase and albumin.

IMMUNOABSORBANTS

The gamma globulin fraction of 5 ml each of human antiserum specific for blood-group A and for B antigens (Spectra Biologicals, Oxnard, Calif., USA) and 10 ml each anti-human serum (Hyland) are prepared by precipitation at 50% saturation with ammonium sulfate at 4° C. The gamma globulin fraction is dialyzed against 0.1 M sodium borate buffer pH 8.2, and covalently coupled to 200 ml of Sepharose 2B (Pharmacia Fine Chemicals, Uppsala, Sweden) activated at pH 11.0 in 0.10 M sodium phosphate with cyanogen bromide (Cuatrecases et al., 1968). The immunoabsorbant containing 4-6 mg. protein/ml agarose beads is retained in a 2.5 $\times$ 60 cm column. A separate immunoabsorbant containing only the gamma globulin from 10 ml of high titer anti-A antiserum is coupled to 50 ml of Sepharose 2B and is used in a 15 $\times$ 30 cm column. The CEA-S$_1$ preparations are passed over these immunoabsorbants at a rate of 4-6 ml/h at 4° C.

ISOPYKNIC DENSITY GRADIENT ULTRACENTRIFUGATION

Preparations are thoroughly dialyzed to water and adjusted to a density of 1.40 with CsCl. Gradients are generated and brought to equilibrium at 76,000 $\times$ g (mean) for 66 h at 20° C. in a Spinco SW-41 rotor. Gradients are eluted in 0.2 ml fractions from the top using an ISCO fractionator. Density is determined in a Bausch and Lomb refractometer and calculated from the Critical Tables. The concentration of CEA-S$_1$ has been estimated from an extinction coefficient E$_{280}$$^{1\%}$ = 5.44) determined gravimetrically from partially purified CEA-S$_1$.

SEDIMENTATION VELOCITY

The sedimentation velocity of radiolabelled purified CEA-S$_1$ is estimated in linear 5 to 25% sucrose gradients (in PBS) at 20° C. $^{125}$I CEA-S$_1$ is mixed with protein standards in 0.2 ml. layered onto 5 ml gradients and centrifuged at 78,000 $\times$ g for 40 h at 20° C. in a Spinco SW SW-50.1 rotor. The gradients are fractionated from the top in 0.2 ml aliquots. Standards consist of purified fibrinogen, $^{131}$I F(ab')$_2$, and fresh serum is used as a source of IgG. The position of fibrinogen and IgG is determined by radial immunodiffusion. CEA-S$_1$ and F(ab')$_2$ are determined by reference to specific radioactivity.

ESTIMATION OF MOLECULAR WEIGHT

Molecular weight is estimated from the Svedberg equation $M = sRT/D(1-v\rho)$, where s equals the sedimentation coefficient ($S°_{20,w}$), D equals diffusion constant ($D°_{20,w}$), $\bar{v}$ equals partial specific volume, $\rho$ equals density of the solution for sedimentation coefficient analysis but has been corrected to 1.00 in the determination of $S°_{20,w}$, R equals the gas constant and T equals absolute temperature. Partial specific volume is estimated as the reciprocal of the observed density of the $^{125}$I labelled molecule upon isopyknic density gradient ultracentrifugation in CsCl.

PREPARATION OF CEA

Conventional CEA is prepared from the PCA-soluble glycoprotein fraction of metastatic adenocarcinoma of the colon by molecular exclusion chromatography on Sepharose 6B (Biorad) followed by Sephadex G-200. One ml samples are fractionated at 8 ml/cm$^2$ cross-sectional area/h on a 2.5 × 80 cm column of Sepharose 6B (Biorad). The effluent is monitored at 280 nm for protein and collected in 5 ml aliquots. Two proteins peaks exhibiting CEA or related antigenic activity are regularly observed as described by Coligan et al (1972). The fraction, with a $S°_{20,w}$ of 6.8, identical with the value described by Coligan et al (1972), is further reisolated at Kd 0.17 from a similar column of Sephadex G-200 and is used as conventional CEA. Preparations of purified CEA were also kindly provided from the laboratory of Dr. C. Todd (City of Hope, Calif. USA) and the British Medical Research Council, National Institute for Biological Standards and Control, Lot 73/601), Holly Hill, London.

POLYACRYLAMIDE GEL ELECTROPHORESIS

Analytical polyacrylamide gel electrophoresis is performed on 5 × 75 mm cylindrical gels utilizing a Bio-Rad Model 150 A apparatus. Discontinuous polyacrylamide gel electrophoresis is performed utilizing both sample and spacer gels under either (1) alkaline conditions in tris-glycine, at pH 8.4 or (2) acid conditions in B-alanine-acetic acid, pH 4.5 as described by Ornstein (1964) using 6% polyacrylamide sample gels. Electrophoresis in the presence of 1% sodium dodecyl-sulfate is performed on 4% polyacrylamide gels according to the method of Weber and Osborn (1969). In each case the gels are sliced into 2 mm sections and the mobility and distribution of $^{125}$I CEA-S are determined by reference to radioactivity.

ASSAY FOR BLOOD GROUP ANTIGENS

The presence of blood-group A and B antigens in preparations is determined by the hemagglutination-inhibition assay using an ultramicrohemagglutination Coombs technique (Linder and Edgington, 1971). The presence of these blood group antigens as well as Rh, Kell, Duffy and Lewis a antigens has been determined by the ability of specific antisera to bind $^{125}$I CEA-S$_1$, $^{125}$I CEA or equivalent preparations.

RADIOIODINATION OF CEA-S$_1$

CEA-S$_1$ is radiolabelled with $^{125}$I by a modified Chloramine-T micromethod (Chisari et al, 1974). As little as 180 ng of CEA-S$_1$ in 1 $\mu$l is effectively labelled to a specific activity of 80–100$\mu$ Ci/$\mu$g. The radioiodinated product retains a density of 1.41 in an isopyknic CsCl density gradient; and more than 97% of the radioactivity is precipitable by 15% trichloracetic acid at 4° C. and by specific antibody. Precipitability does not deteriorate on storage for at least two months.

ANTISERA

Antiserum to CEA is prepared in rabbits by primary immunization with (a) 600 $\mu$g of the PCA-soluble glycoprotein fraction or (b) 50 $\mu$g purified CEA emulsified in complete Freuend's adjuvant which is injected in the rear footpads. Subsequent booster immunizations of the same dose are given in incomplete adjuvant in multiple subcutaneous sites at 3- to 4-weekly intervals. Antiserum for this study has been collected at 2-3 months and later in the response and rendered specific by exhaustive absorption with normal human serum, normal erythrocyte stroma, porcine and equine soluble blood-group A and B substances, (Dade, Miami, Fla., USA) and lyophilized homogenates of normal adult colon, lung and liver. This anti-serum, anti-CEA, is monospecific by Ouchterlony gel diffusion against the crude saline tumor extract, the PCA-soluble glycoprotein fraction, conventional CEA or partially purified CEA-S$_1$ recovered from the immunoabsorbant column. This antiserum forms a line of identity with that (anti-CEA$_M$) kindly provided by Dr. J. P. Mach (University of Lausanne, Switzerland), an antiserum which was compared with the original anti-CEA antiserum of Gold, et al. The above antiserum binds radiolabelled CEA-S$_1$, conventional and purified CEA$_{(Be)}$ from the laboratory of Dr. C. Todd (City of Hope, California, USA). radioimmunoassay.

Hyperimmune antiserum to rabbit IgG is produced in goats immunized subcutaneously on a monthly schedule with 100 $\mu$g of rabbit IgG in incomplete adjuvant. The antiserum is adjusted to an antigen binding capacity at equivalence of ~0.6 mg IgG/ml for use as the second antibody in the double antibody radioimmunoassay.

ANTIGEN BINDING RADIOIMMUNOASSAYS

The capacity of antisera to bind CEA-S$_1$ is determined by radioimmunoassay consisting of: (1) 0.25 ml of $^{125}$I CEA-S$_1$ (0.18 ng) in 1:33 normal rabbit serum, 0.14 M NaCl, 0.1 M sodium borate pH 8.2 (RSB): (2) 0.25 ml of serial dilutions from 1:33 of the anti-CEA antiserum in RSB: and (3) 1.0 ml 0.14 M NaCl, 0.1 M sodium borate, pH 8.2 (BB) in a 12 × 75 mm tube. Following 18-20 h incubation at 4° C., (4) 0.50 ml of goat anti-rabbit IgG second antibody diluted in BB is added and incubated 5 h at 4° C. Phase separation is accomplished by centrifugation at 1,500 × g for 20 min, and 1.0 ml of supernatant is sampled and counted to determine free $^{125}$I CEA-S$_1$. The bound/free ratio is also calculated.

COMPETITIVE INHIBITION ASSAY OF CEA-S$_1$

CEA-S$_1$ is assayed by equilibrium competitive inhibition radioimmunoassay of double antibody type similar to that previously described (Plow and Edgington, 1973a), modified with respect to compartment volume and reagent concentrations. Test samples are used directly except for serum which is first clarified at 7,000 × g for 10 min. The assay is performed in duplicate and consists of: (1) 0.33 ml of sample which is transferred with 0.67 ml of BB to 12 × 75 mm tubes; (2) 0.25 ml of $^{125}$I CEA-S$_1$ (0.18 ng) in RSB; and (3) 0.25 ml of anti-CEA antiserum diluted in RSB to give 50–60% binding of $^{125}$I CEA-S$_1$. Following 18 h incubation at 4–6° C., (4) 0.50 ml of anti-rabbit IgG second antibody is added. After an additional 5 h incubation at 4–6° C. the tubes are centrifuged at 1,500 × g for 20 min. One ml of supernatant is transferred to fresh tubes and counted for $^{125}I$. Controls include trichloric acid precipitable control for maximum precipitation, and no anti-CEA and no precipitating antibody controls for minimum Precipitation. Data are processed and reduced to $^{125}I$ CEA-$S_1$ bound/free ratio, which in turn is plotted against an arbitrary CEA-$S_1$ standard. This standard consists of an ultracentrifugally clarified saline extract of a lyophilized homogenate of an adenocarcinoma of the colon. It is given a value of 33,300 units/ml. The inhibition profile is linear over the range ~6 to ~90 units/ml when plotted against the log of competing antigen concentration. The coefficient of variation of the assay, at 13.9 units/ml, is 6.5%.

Soluble tissue constituents were extracted from tumors by homogenization, incubation in 1M NaCl, which are equivalent, and and clarification by ultracentrifugation.

Twelve preparations from primary colonic adenocarcinomas reacted with anti-CEA by gel diffusion and gave concentrations of CEA-$S_1$ varying from 2,900 to 59,840 units/g and a mean concentration of 30,633 units/g tumor. Metastatic adenocarcinomas contained an average of 6,700 units CEA-$S_1$/g tumor. Subsequent addition of perchloric acid at concentrations from 0 to 2.0 M demonstrated no significant loss of CEA-$S_1$ from the dialyzed supernatant. A concentration of 0.90 M perchloric acid as described by Krupey et al (1968) was accepted and utilized in this study. Subsequent studis have employed 0.60 M PCA.

When such glycoprotein preparations were fractionated on isoelectric focusing columns, marked heterogeneity of net molecular charge was observed for the prototype preparation (Plow and Edgington, Int. J. Cancer:15, at p. 753). Four major CEA related glycoprotein fractions were recovered in pH 3–6 gradients. These had isoelectric points of approximately 3.8, 4.1, 4.5 and 5.4 with the prototype preparation; the pI 4.5 peak appeared to consist of three components recognized by monitoring of trechloracetic acid precipitate or by optical density at 280 nm. Each of these species of CEA exhibited apparent gross immunochemical identity by gel diffusion against anti-CEA. Significant differences have been observed between protein peaks detected at 280 nm and those detected by reference to $^{125}I$, indicating that different species of glycoproteins are radioiodinated to a different extent. In this respct, a minor pI 5.4 CEA species was virtually unlabelled. CEA-related material isolated from the gradient in the vicinity of pH 4.5 has been utilized for isolation of CEA-$S_1$.

The pH 4.25–4.80 fraction of preparation has been fractionated into several sizes of glycoproteins by molecular exclusion chromatography on A 1.5 fine then on Sephandex G-200. The second peak of CEA from A 1.5 fine (sedimentation velocity approximately 6.8) has been utilized for subsequent purification, though the first peak is also reactive with anti-CEA anti-sera in gel diffusion assay and radioimmunoassay for CEA. The second and major peak with a Kd of 0.17 from Sephadex G-200 has been retained for subsequent isolation. This fraction has been resolved into two major fractions as well as minor fractions by ion-exchange chromatography on DEAE-cellulose using 0.05 M $Na_2HPO_4$ as the equilibration and eluting buffer, as exemplified by the prototype preparation. The initial fraction of the applied glycoprotein was retarded only slightly by the resin, and two minor fractions as well as a major component were recovered by further elution with 0.50 M $NaH_2PO_4$.

The partially purifid CEA-$S_1$ has been subjected to two passages through immunoabsorbant columns containing antiserum to human serum and to blood-group antigens A and B. Preparations with high concentrations of A-like antigen have required additional passages through separate anti-A immunoabsorbant columns to achieve complete removal of all detectable A-like antigen. Table 1 summarizes the sequential removal of A-like antigen from prototype CEA-$S_1$. Material bound by the immunoabsorbant and subsequently eluted with 3 M potassium iodide, pH 7.4, did not possess significant CEA-$S_1$ by radioimmunoassay though the recovered CEA-$S_1$ fraction was highly reactive by both radioimmunoassay and gel diffusion using anti-CEA antiserum.

Table 1

| | Removal of Blood-Group A Related Antigen From Prototype CEA-$S_f$ by Immunoabsorbants | |
|---|---|---|
| Passage | Immunoabsorbant | A antigen[1] (titer) of preparation |
| None | None | 1:128 |
| 1 | I Anti-A, anti-B, antiserum | 1:32 |
| 2 | I Anti-A, anti-B, antiserum | 1:16 |
| 3 | II Anti-A | 1:4 |
| 4 | II Anti-A | Neg |

[1]Titer of sample (5 μl) required to neutralize anti-A antiserum (1 μl) with a titer of 1:512.

Final purification of CEA-$S_1$ recovered from the immunoabsorbants has been achieved by isopyknic density gradient ultracentrifugations in CsCl. After 66 h of centrifugation at 76,000 × g in a Spinco SW-41 rotor, three components of mean density <1.30, 1.41 and 1.52 were resolved for the prototype preparation. The relative distribution of the three components has varied with preparations from different tumors due to the degree of glycosylation of different species of CEA. The peak extending from 1.37 to 1.45 g/ml with a mean density of 1.41 g/ml is retained as purified CEA-$S_1$. The peak of higher density, although reactive with anti-CEA, was relatively less reactive in assay of CEA-$S_1$. The approximate recovery of glycoprotein in CEA-$S_1$ fractions from each purification relative to the PCA extract is summarized in Table II. The final recovery of CEA-$S_1$ from this tumor has represented less than 2.0% of the radioiodinated glycoprotein present in the PCA-soluble tumor extract.

Table II

| Relative Recovery of CEA-$S_f$ Containing Fractions from PCA-Soluble Tumor Glycoprotein (Tumor #1) | |
|---|---|
| Procedures | Recovery[1] (%) |
| (1) Isolectric focusing | 55 |
| (2) Molecular exclusion | 43 |
| (3) Ion exchange | 52 |
| (4) Immunoabsorbant | 58 |
| (5) Isopyknic density gradient | 25 |
| Final recovery | 1.8 |

[1]Recovery is calculated at the % of the applied $^{125}I$ glycoprotein radioactivity recovery in the CEA-$S_f$ pool from each purification procedure. Recovery differs with different tumors and is comparable when analyzed by absorbance of 280 nm for proteins.

Certain features of CEA-$S_1$ have been established by reference to behavior during isolation, i.e., CEA-$S_1$ has a pI of approximately 4.5, a buoyant density of 1.41 g/ml and is not associated with blood-group antigens A or B, Rh, Kell, Duffy or Lewis (Le -a). The homogeneity of CEA-$S_1$ in acid, alkaline and SDS polyacrylamide gels was demonstrated by polyacrylamide gel electrophoresis of purified $^{125}$I CEA-$S_1$ in 5 × 75 mm cylindrical gels using a 4% gel in the presence of 1% sodium dodecyl sulfate, a 6% discontinuous gel in B-alanine acetic acid pH 4.5, and a 6% discontinuous gel in trisglycine, pH 8.4. (Plow and Edgington, Int. J. Cancer: 15, at p. 756) Under each analytical system CEA-$S_1$ migrated as a single discrete band, and more than 85% of the applied radioactivity was recovered in the single symmetrical band. In sucrose density gradients, CEA-$S_1$ sedimented as a discrete and homogeneous species. On the basis of its behavior relative to proteins with known sedimentation coefficients, a $S_{20,w}$ of 6.6 was estimated for CEA-$S_1$ using sedimentation velocity untracentrifugation of $^{125}$I CEA-$S_1$ in a 5 to 25% sucrose gradient. The ultracentrifugation was performed in a SW-50.1 Spinco rotor at 78,000 × g at 20° C. for 40 h. Protein standards utilized to estimate the $S_{20,w}$ of CEA-$S_1$ were included in the same tube and were fibrinogen IgG and F(ab')$_2$ fragment of IgG. The diffusion constant and mean Stokes radius of CEA-$S_1$ were analyzed from molecular exclusion behavior on Sephadex G-200 (Siegel and Monty, 1966). By means of such calibrated columns a Kd of 0.17 was determined for CEA-$S_1$ graphically. The Kd of CEA-$S_1$ and standard proteins-fibrinogen, catalase and albumin were determined by molecular exclusion chromatography in Sephadex G-200. The Kd or derivative (Kd)$^{1/3}$ was plotted against established diffusion constants and Stokes radii of the standard proteins. CEA-$S_1$ has an estimated diffusion constant ($D_{20,w}$) of 3.05 × 10$^{-7}$ cm$^2$sec and mean Stokes radius of approximately 65 A. The molecular parameters of CEA-$S_1$ determined in this study are summarized in Table III.

Table III

| Summary of The Molecular Parameters Of CEA-$S_1$ | |
|---|---|
| Physical constant | Value |
| pI | 4.5 |
| $S_{20,w}^o$ | 6.6 |
| Kd (G-200) | 0.17 |
| $D_{20,w}^o$ | 3.05 × 10$^{-1}$ cm$^2$/sec |
| Stokes radius | 65 A |
| $\rho$ | 1.41 g/ml |
| v | 0.709 ml/g |
| M | 181,000 |

Immunochemical characterization of CEA-$S_1$ was performed in double antibody radioimmunoassays utilizing $^{125}$I-CEA-$S_1$ as the ligand and anti-CEA. The ligand was completely bound by antiserum at a dilution of 1:50 of anti-CEA antiserum and on serial dilution of the antiserum a typical semilogarithmic binding profile with a single component was generated, suggesting the presence of only one antigenic species in the ligand. In competitive inhibition immunoassays binding of the ligand was completely inhibited by: (1) standard tumor extracts; (2) serum from a patient with adenocarcinoma of the colon; (3) conventional CEA; and (4) purified CEA-$S_1$. Slight differences in competitive inhibition slopes of the competing antigens were within the precision of the assay and suggest that the qualitative antigenic expression of CEA-$S_1$ in each of these materials is similar if not identical. (Plow and Edgington, Int. J. Cancer: 15, at p. 758) Significant quantitative differences were observed in the immunochemical expression of conventional CEA as compared to CEA-$S_1$. Identical results were obtained also with different preparations of conventional CEA including preparations Be from the laboratory of Dr. C. Todd and standard CEA prepared by the British Medical Research Council. As compared to the arbitrary CEA-$S_1$ standard, a purified preparation of CEA-$S_1$, standardized by reference to absorbance at 280 nm, gave a value of 0.64 ng/unit CEA-$S_1$ whereas several preparations of CEA required an approximately 5.26 times greater concentration to produce equivalent 50% competitive inhibition. This was equivalent to 3.37 ng CEA/unit of CEA-$S_1$.

DISCUSSION

Characterization of CEA by Krupey et al. (1968) suggested that such preparations contained a single homogeneous glycoprotein. Homogeneity of conventional CEA preparations was suggested by the studies of Terry et al. (1972) which demonstrated that the major protein constituent of five preparations from different colonic tumors possessed identical sequences through the first 24 amino acid residues. Subsequent studies have demonstrated that preparations of CEA exhibit heterogeneity with respect to a number of analytical parameters. Upon isoelectric focusing (Rule and Goleski-Reilly, 1974) and ion exchange chromatography (Coligan et al., 1973; Eveleigh, 1974), preparations of purified CEA have been resolved into multiple species; and even in the analysis of a preparation of CEA homogeneous with respect to isoelectric point, Turner et al. (1972) observed three discrete components differing in density by isopyknic density gradient ultracentrifugation. Heterogeneity of CEA has also been demonstrated with respect to the expression of blood-group-related antigens; some preparations of CEA appear to be essentially devoid of A-like blood-group determinants, while in other studies blood-group antigens appear to be present on the same molecule expressing CEA determinants (Gold and Gold, 1973; Simmons and Perlmann, 1973). It has been suggested that CEA also possesses blood group Lewis a (Le-a) antigen. (Holburn, A.M. et al, Immunology 26: 831–843, 1974.) Furthermore, since CEA is defined immunochemically, normal serum and tissue constituents which share antigenic determinants and exhibit varying degrees of immunochemical cross reaction with CEA (Mach and Pusztaszeri, 1972; von Kleist et al., 1972) might also be considered as potential heterogenous species of CEA. The molecular basis and significance of the observed heterogeneity have not been established. Although variation in content of N-acetyl neuraminic acid does influence behavior in charge-related analytical systems, following complete removal of N-acetyl neuraminic acid some residual heterogeneity can still be demonstrated (Coligan et al., 1973). Further, removal of N-acetyl neuraminic acid from CEA does not render it equivalent to CEA-$S_1$ in immunochemical reactivity. (Edgington, T.S. and Plow, E.F, unpublished).

The previously described heterogeneity of CEA-related glycoproteins with respect to isoelectric point, behavior in ion exchange and density has been observed in the isolation of CEA-$S_1$ and additional degrees of heterogeneity have been established. The demonstration that CEA-related glycoproteins with a specific isoelectric point can be further fractionated by ion exchange chromatography indicates that heterogeneity of these molecules must reflect differences between species in local charge density as well as net molecular charge. The resolution of CEA into three components by isopyknic density gradient ultracentrifugation following the removal of blood-group A-like activity via immunoabsorption indicates that the presence of a species with a density of 1.52 g/ml is not dependent only upon blood-group activity as previously suggested by Turner et al. (1972). The recovery of CEA-$S_1$ from anti-A immunoabsorbant columns establishes that CEA and blood-group A determinants can reside on independent molecules. Although some previous preparations of CEA have been reported to be devoid of blood-group activity, the presence of blood-group antigens may reflect only the blood type of the donor rather than any effective or specific removal of these blood-group-related molecules during purification.

A molecular weight of 181,000 has been calculated for CEA-$S_1$ according to the Svedberg equation. To obtain this value, it has been necessary to assume that the buoyant density of CEA-$S_1$ in cesium chloride reflects the true partial specific volume of the molecule, that the diffusion constant estimated from the Kd of CEA-$S_1$ on Sephadex G-200 was not altered by interactions with the gel matrix, and that the sedimentation of CEA-$S_1$ in sucrose accurately reflects the sedimentation coefficient of the molecule. In simultaneous parallel analyses in sucrose gradient, a sedimentation coefficient of 6.8 S was determined for conventional CEA, a value identical to that reported by Coligan et al. (1972) which supports the validity of the 6.6 S value of CEA-$S_1$. The $\bar{v}$ of 0.709 ml/g determined by ultracentrifugation in cesium chloride and provides the only currently available estimate for CEA-$S_1$. Molecular weights of conventional CEA of approximately 200,000 to 300,000 daltons have been suggested (Coligan et al., 1972; Pusztaszeri and Mach, 1973); however, these estimates are based solely on molecular exclusion properties, a particularly unreliable approach with glycoproteins (Winzor, 1969). The similarity in sedimentation and gel filtration properties on G-200 for CEA and CEA-$S_1$ suggests that these previous estimates may be high. Although CEA-$S_1$ may be smaller than conventional preparations of CEA based on the slight differences in sedimentation coefficients, it is still significantly larger than described molecules that cross-react with CEA (Mach and Pusztaszeri, 1972; von Kleist et al., 1972; Burtin et al., 1973; Newman et al., 1974).

Immunochemical analyses utilizing the $^{125}$I-CEA-$S_1$ ligand (Edgington and Plow, U.S. Pat. application Ser. No. 682,027 Filed Apr. 30, 1976, concurrently herewith, and Edgington, Astarita and Plow, New Eng. J. Med., 293: 103–107 (July 17, 1975) ) provide further basic information concerning the isolated molecule and establish its relationship to conventional CEA. First, these analyses indicate that CEA-$S_1$ as isolated is antigenically comparable to those molecules present in tumors and the serum of certain cancer patients recognized by anti-CEA. The capacity of equilibrium competitive inhibition radioimmunoassays to discriminate minor structural differences has been well documented (Plow and Edgington, 1972, 197 3b; Edgington and Plow, 1975); and the similarity in competitive inhibition slopes of these samples indicates that, despite the extensive handling of CEA-$S_1$ in isolation, the molecule must remain quite similar to molecules present in vivo. Second, the capacity of conventional CEA and CEA-$S_1$ to yield complete competitive inhibition and generate curves with similar slopes strongly supports the concept that CEA-$S_1$ is a species of CEA. Third, the 5.26-fold difference in the quantitative expression of CEA and CEA-$S_1$ indicates that this isolated and characterized species of CEA is not immunochemically identical to the CEA glycoprotein set but must represent a specific isomer, a concept similar to that developed in studies of enzyme sets and their constituent isoenzymes. By inference other isomers of CEA must also be immunochemically distinct from CEA-$S_1$.

RADIOIMMUNOASSAY

Serum was directly assayed in duplicate for CEA-$S_1$ by equilibrium competitive inhibition radioimmunoassay of double-antibody type (J. Clin. Invest. 52: 273–282, 1973), modified for compartment volume (Int. J. Cancer, 15: 748–761, 1975), with use of a Micromedic automated pipetting station. Test serum was clarified at 7000 $\times$ g for 10 minutes, and 0.33 ml was transferred with 0.67 ml of borate buffer (0.14 M sodium chloride and 0.10 M sodium borate, pH 8.2) to tubes 12 $\times$ 75 mm. To this mixture was added 0.25 ml of $^{125}$I-CEA-$S_1$ (180 pg at 100 $\mu$ Ci per microgram) in diluent (1:33 normal rabbit serum in borate buffer) and 0.25 ml of rabbit anti-CEA antiserum diluted to give approximately 55 per cent binding of the $^{125}$I-CEA-$S_1$. After incubation for 18 hours at 4° C., 0.50 ml of hyperimmune goat anti-rabbit IpG, in mild antibody excess, was added. After a five-hour incubation at 4° C. the tubes were centrifuged for 20 minutes at 1500 $\times$ g; 1.00 ml of supernatant was automatically transferred to fresh tubes and counted for $^{125}$I. Data were processed by computer program, and were reduced to ratio of bound to free $^{125}$I-CEA-$S_1$. S. This ratio was plotted against dilusions of an arbitrary CEA-$S_1$ standard, an ultracentrifugally clarified saline extract of a lyophilized homogenate of an adenocarcinoma of the colon, which was arbitrarily given a value of 33,300 units of CEA-$S_1$ per milliliter. The linear portion of the inhibition profile, employed for analysis, usually extended from approximately 6 to approximately 90 units of CEA-$S_1$ per milliliter (New Eng. J. of Med., 293: at P. 104). The average of the duplicate values was accepted if within 10 per cent. Approximately 8 per cent of serum specimens fall in the range of 12 to 19 units, and these were repeated. The coefficient of variation of the assay was 6.5 per cent at 13.9 units of CEA-$S_1$ per milliliter. One unit of CEA-$S_1$ appears to be equivalent to approximately 0.64 ng of purified CEA-$S_1$; whereas preparations of purified conventional CEA 3.0 to 10.4 times greater were required for equivalent competitive inhibition.

PATIENT SELECTION

Nine hundred and ninety-three patients were accepted for the study. The 268 patients with neoplastic disease included 138 with adenocarcinoma of the stomach, exocrine pancreas, colon and rectum as well as 130 other forms of cancer. Normal levels of serum CEA-$S_1$ were evaluated in a series of 435 random hospital and clinic patients without evidence of neoplasia during a subsequent two-year follow-up period. An additional 290 patients with non-neoplastic disease were studied. including 147 patients hospitalized with gastrointestinal inflammatory diseases (peptic ulcer, regional enteritis, acute pancreatitis, gastritis, diverticulitis, multiple colonic polyposis, and chronic ulcerative colitis). The diagnosis was made, and severity was classified on the basis of the severity of diarrhea, anemia, fever, leukocytosis and particularly sigmoidoscopic and radiologic examinations. Of 13 serums from this group, 11 had levels of carcinoembryonic antigen $\geq$ 2.5 ng per milliliter, and six levels $\geq$ 5.0 ng per milliliter as measured by the Hoffman-LaRoche (Nutley, N.J.) Zirconyl phosphate method. Sixty-seven patients with liver disease included 47 with severe cirrhosis, predominantly alcoholic, with decompensation characterized by jaundice, hypoalbuminemia, encephalopathy or coma. Of four serums sampled from this group all had levels of carcinoembryonic antigen greater than 2.5, and two were $\geq$ 5.0 ng per milliliter. Of the 34 patients with chronic renal disease, 28 were maintained on dialysis. Forty-two patients with other diseases, including rheumatoid arthritis, pulmonary emphysema, chronic brochitis, scleroderma and myocardial infarction were evaluated.

CORRELATION BETWEEN CEA-$S_1$ AND CARCINOEMBRYONIC ANTIGEN

Parallel analyses of CEA-$S_1$ and carcinoembryonic antigen were performed on 21 serum specimens from patients with cancer of the gastrointestinal tract, lung or breast, and on 19 patients with chronic ulcerative colitis or advanced liver disease, and on plasma to which standard tumor extract had been added. The zirconyl phosphate method (Hoffman-LaRoche, Nutley, New Jersey) was used for determination of carcinoembryonic antigen (N. Engl. J. Med. 285: 138–141, 1971).

STATISTICAL ANALYSES

Statistical analyses were performed on Texas Instruments SR-51 and Wang 462 programmable calculators. Values are given as arithmetic means $\pm 1$ standard deviation. Comparisons of CEA-$S_1$ and carcinoembryonic antigen employed linear regression analysis, calculation of correlation coefficient (r) and statistical significance by two tailed t-test. The frequency of elevated CEA-$S_1$ in the various groups was analyzed by chi-square analysis.

RESULTS

CEA-$S_1$ or related glycoproteins were detectable at low concentration in the serum of normal controls and patients. The validity of the observed low levels of CEA-$S_1$ s in these serum specimens was confirmed by assay of 20-fold to 50-fold concentrates of 0.9 M perchloric acid soluble glycoprotein fractions of 11 plasmas and serums. The quantity of CEA-$S_1$ in the concentrates was adequate to permit accurate assay, and the inhibition slope of the concentrated normal sera were similar to those of the tumor standard and CEA-$S_1$ positive serums. The means and standard deviation was 1.52 + 0.15 unit of CEA-$S_1$ per milliliter and included samples of each of the ABO blood groups.

The mean concentration of CEA-$S_1$ in serums from 435 random clinic admissions (patients without evidence of neoplasia) was 3.62 $\pm$ 3.46 units per milliliter. A normal range of 0 to 13.9 units per milliliter (mean $\pm$ 3 standard deviations) should statistically encompass the normal population at the 99.7 per cent level of confidence. Adoption of this range of normal provided an observed true-negative frequency of 99.7 per cent and a false-positive rate of 0.23 per cent among random patients without evidence of neoplasia.

No significant correlation was observed between carcinoembryonic antigen and CEA-$S_1$ in normal plasma with added standard tumor extract. The correlation coefficient ($\gamma$) was $-0.33$. Nor was there significant correlation for serums from patients with chronic ulcerative colitis and liver disease, $r = -0.11$ In contrast a significant correlation between levels of CEA and CEA-$S_1$ was observed in a panel of serums from patients with cancer of the gastrointestinal tract, lung and breast ($r=0.93, P<0.01$).

The association of CEA-$S_1$ with adenocarcinoma of the colon was demonstrated by the presence of concentration of CEA-$S_1$ $\geq$ 14 units per milliliter in the serum of 86 per cent of 90 patients with this tumor, see Table 1.

Table 1

| Frequency of Elevated Levels of CEA-$S_I$ in the Serum of 268 Patients with Tumors | | | |
|---|---|---|---|
| | | Elevated Serum CEA-$S_I$* | |
| Location of Tumor | No. of Patients | No. of Patients | % |
| Gastrointestinal tract: | | | |
| Colon | 90 | 77 | 85.6 |
| Rectum | 24 | 14 | 58.3 |
| Stomach | 11 | 8 | 73.0 |
| Pancreas, exocrine | 13 | 12 | 92.0 |
| Islet-cell tumors of pancreas | 2 | 0 | 0 |
| Lung | 26 | 3 | 11.5 |
| Breast | 45 | 7 | 15.6 |
| Other | 57 | 2 | 3.5 |

*Serum CEA-$S_I$ $\geq$ 14.0 U/ml.

CEA-$S_1$ was less frequently elevated in adenocarcinomas of the rectum (58 per cent), possible owing to the higher frequency of early clinical recognition of these tumors. The 73 per cent rate of elevated CEA-$S_1$ in association with adenocarcinoma of the stomach is not significantly different from that of the colon (p > 0.3).

CEA-$S_1$ was clearly elevated in 12 of 13 cases of carcinoma of the exocrine pancreas, though present at normal concentrations in four patients with acute pancreatitis. Endocrine tumors of the pancreas were not associated with elevated CEA$_1$. Among 130 patients with tumors extrinsic to the gastrointestinal tract, elevated serum CEA-$S_1$ was observed at a significantly lower frequency (15.6 per cent) in carcinoma of the breast (P < 0.0001) and carcinoma of the lung (11.5 per cent; P < 0.001). Only two of 57 patients with other types of tumors has positive results (P < 0.001). These findings suggest moderate specificity of CEA-$S_1$ for tumors of the gastrointestinal tract.

A relation between the mass of tumors and the concentration of CEA-$S_1$ is suggested from study of two groups of patients with adenocarcinoma of the colon or rectum, as shown in Table 2.

Table 2

| Relation between Clinical Evidence of Metastasis of Adenocarcinomas of the Colon and Rectum and Levels of CEA-$S_I$ in Serum | | | |
|---|---|---|---|
| Evidence of Metastasis | No. of Patients | % With Elevated Serum CEA-S* | Mean CEA-$S_I$ Concentration U/ml |
| Established | 49 | 91.8 | 135.0 |
| Not established | 41 | 75.6 | 37.7 |

*Serum CEA-$S_I$ $\geq$ 14.0 U/ml

Among patients with clinically established metastases 91.8 per cent had positive results, and the mean concentration was 135 units of CEA-$S_1$ per milliliter, whereas mong patients without clinically established metastatic tumor only 75.6 per cent had elevated CEA-$S_1$ The mean concentration of patients in the latter group was 37.7 units of CEA-$S_1$ per milliliter of serum. These results suggest a relation between the mass of tumor and the serum level of $CEA_{S1}$.

With 14 units per milliliter used as a diagnostic threshold, the concentration of $CEA-S_1$ in the serum of 290 additional patients comprising four non-neoplastic disease groups was evaluated, see Table 3.

Table 3
Frequency of Elevated Levels of $CEA-S_1$ in 725 Patients With Non-neoplastic Diseases

| Group | No. of Patients | % With Elevated Serum $CEA-S_1$* |
|---|---|---|
| Random subjects | 435 | 0.23 |
| Gastrointestinal inflammatory disease | 147 | 0.68 |
| Chronic ulcerative colitis, total | 53 | 1.9 |
| Chronic ulcerative colitis, severe | 22 | 4.5 |
| Acute pancreatitis | 4 | 0 |
| Liver disease, total | 67 | 1.5 |
| Advanced cirrhosis | 47 | 2.1 |
| Advanced renal disease | 34 | 0 |
| Other disease | 42 | 0 |

*Serum $CEA-S_1 \geq 14.0$ U/ml.

Only one of the 147 patients with inflammatory disease of the gastrointestinal tract had a marginal elevation of serum $CEA-S_1$ to 15.1 units per milliliter. This patient had severe chronic ulcerative colitis, and no evidence of neoplasia was found on post-mortem examination. None of the 52 other patients with chronic ulcerative colitis had elevated serum levels of $CEA-S_1$ although six of 16 of them had CEA concentrations greater than 5.0 ng per milliliter. Among 67 patients with liver disease, only one of 47 with advanced cirrhosis had an elevated $CEA-S_1$ (16.5 units per milliliter). Of four serums from this group carcinoembryonic antigen was greater than 2.5 ng per milliliter in all and greater than 5.0 ng per milliliter in half. None of the 34 patients with advanced renal disease and none of 42 with other diseases had elevated serum $CEA-S_1$.

DISCUSSION

The search for molecular markers of the neoplastic cell has led to recognition of a number of tumor-associated antigens, including oncofetal antigens, molecules characteristic of fetal differentiation. Carcinoembryonic antigen, a widely studied oncofetal antigen localized predominantly in the gastrointestinal tract, is present at elevated concentrations in the serum of the majority of patients with adenocarcinoma of the gastrointestinal tract. Although the association of carcinoembryonic antigen with gastrointestinal tumors has been well established, it has also been demonstrated in the serum of patients with a variety of other tumors. The diagnostic usefulness has been limited by the demonstration of carcinoembryonic antigen at elevated concentration in the serum of 3 to 18 per cent of normal persons and in association with a wide variety of non-neoplastic diseases, notably liver disease, inflammatory bowel disease and chronic renal disease.

Contrary to the early impression that carcinoembryonic antigen represented a single homogeneous glycoprotein recent studies have demonstrated biochemical heterogeneity. The isoelectric profile of carinoembryonic antigen extracted from tumors has been shown to differ from that extracted from fetal or embryonic tissue, and six or more molecular species of carcinoembryonic-like antigen species have been observed. The basis for this heterogeneity has not been fully established, although variations in sialic acid content may be partially responsible. The observed heterogeneity introduces the possibility that carcinoembryonic antigen, as currently defined, does not represent a single molecular entity but rather a set of related or isomeric glycoproteins sharing certain sets of antigenic determinants.

We have identified and described the isolation and characterization of a single homogeneous isomeric species of carcinoembryonic antigen. This molecule, referred to as $CEA-S_1$, represents a pI 4.5 isomer of carcinoembryonic antigen, an isoelectric form of particular prominence in extracts of colonic adenocarcinomas. This glycoprotein with an estimated molecular weight of 181,000 shares antigenic determinants with carcinoembryonic antigen but is devoid of blood-group antigens, and radioimmunoassay exhibits preferential specificity for $CEA-S_1$ as compared to preparation of carcinoembyonic antigen.

Elevated levels of $CEA-S_1$ were observed in the serum of most patients with gastrointestinal tumors, and in a sample of patients with neoplasia a significant correlation between carcinoembryonic antigen and $CEA-S_1$ was observed, $= +0.93$ ($P < 0.01$). A somewhat lower incidence of elevated serum $CEA-S_1$ was found in patients with adenocarcinoma of the rectum, which may reflect earlier clinical recognition of these tumors. Although detection of elevated serum $CEA-S_1$ in patients with adenocarcinoma of the gastrointestinal tract is similar to that reported for carcinoembryonic antigen, $CEA-S_1$ is rarely elevated in association with carcinoma of the breast or the lung, tumors frequently associated with elevated concentrations of carcinoembryonic antigen.

Although the frequency of elevation of carcinoembryonic antigen and CEA-S may be similar in gastrointestinal cancer, greater specificity of $CEA-S_1$ for neoplasia is clearly evident from the study of patients with non-neoplastic diseases. Carcinoembryonic antigen has been elevated in the serum of 2 to 70 per cent of patients with alcoholic liver disease, 11 to 41 per cent with chronic ulcerative colitis, and 54 per cent with chronic renal failure. In contrast, only rare patients with these diseases have elevated levels of $CEA-S_1$, and parallel analysis of a sample including chronic ulcerative colitis and liver disease demonstrated no statistical correlation between the concentration of $CEA-S_1$ and CEA )r = $-0.11$). In the present study, elevated concentrations of $CEA-S_1$ were associated with neoplasia in 97.6 per cent of 126 such patients; the incidence of false-positive results was only 0.41 per cent in a population heavily weighted with diseases usually associated with elevated carcinoembryonic antigen.

The present study is consistent with biochemical and immunochemical features suggesting that $CEA-S_1$ represents an isomeric species of carcinoembryonic antigen, and further that it may be a tumor-dominant form of this set of oncofetal molecules. Structural studies may elucidate the molecular basis for the unique immunochemical features of $CEA-S_1$ and the biologic implications of its association with the neoplastic cell. The improved specificity achieved by assay of $CEA-S_1$ facilitates current improvements in detection of neoplasia in patients pre-disposed to gastrointestinal neoplasia as well as the differential diagnosis and management of these forms of cancer.

In one aspect the invention is a new radioimmunoassay reagent, radiolabelled isolates of carcinoembryonic antigen species, here denominated $CEA-S_1$ and for further reference to distinguish this from all other possible species denominated CEA-S$_1$, isolated and concentrated from glycoprotein extract of human adenocarcinomas of the intestinal tract useful in diagnostic procedures. In the diagnosis of cancer of the human gastrointestinal tract the concentrate of isolated CEA-S$_1$ may be tagged for detection by radiolabelling with $^{125}$I or a number of other convenient labels. Other important reagent results from fluorescein labelling of CEA-S$_1$ with fluorescence detection enzymes for enzymatic detection, etc. CEA-S$_1$ may also be used directly in visible agglutination diagnostic tests according to known and published techniques. CEA-S$_1$ may be used to raise anti-CEA-S$_1$ antisera for use in immunodiagnostic assay and also for immunochemical purification of antibodies used in various immunodiagnostic assays including:

(a) radioimmunoassays of competitive inhibition type and radiometric (sandwich) type;

(b) immunohistochemical analysis of body fluids and tissues; and (c) various forms of particle radioautographic enzymatic and fluorescence assays of tissue or with extracts.

At present, use of CEA-S$_1$ as a radioimmunoassay reagent in most advantageous using the equipment available to the inventors; however, the form in which CEA-S$_1$ is used as a diagnostic reagent depends upon the equipment available to a particular worker and upon the personal preferences and experience of the worker.

The new concentrated and isolated $^{125}$I-CEA-S$_1$ is characterized by a number of physicochemical constants and by immunochemical reactions. Among the distinguishing physicochemical constants are the following.

Sedimentation velocity of CEA-S$_1$ and $^{125}$I-CEA-Sas measured by the standard sucrose gradient test, using linear 5 to 25% surcrose gradients in PBS at 20° C., S°$_{20,w}$, is 6.6 Svedberg units compared with 6.8 for $^{125}$I-CEA. While the absolute value in Svedberg units could vary between laboratories, apparently as a result of minor difference in techinque and instrumentation, $^{125}$I-CEA-S$_1$ has to date demonstrated a sedimentation velocity about 2 to 4 percent lower than the sedimentation velocity of $^{125}$I-CEA measured comparatively, using the same technique and instrumentation.

Isoelectric point is another distinguishing feature of $^{125}$I-CEA-S-$_1$. First, $^{125}$I-CEA-S$_{1b}$ is distinct from $^{125}$I-CEA in that $^{125}$I-CEA-S$_1$ is demonstrated by isoelectric point to be a single distinct species producing a single distinct isoelectric point, pI = 4.5 ± 0.1, whereas $^{125}$I-CEA produces, in comparative tests using the same technique and instrumentation, a variable distribution from about pI = 3 to about pI = 4.2. pI for $^{125}$I-CEA-S$_1$ will always produce a single discrete isoelectric point having a value of from about pI = 4.4 to about pI = 4.6.

Buoyant density also serves to distinguish $^{125}$I-CEA-S$_1$ from $^{125}$I-CEA. Turner et al (J. Immunol., 108, 1328–1339, 1972) reported three bands of density in CEA-S$_1$, 1.47, 1.42 and 1.28, but until the present work of isolation and concentration no single species $^{125}$I-CEA has been heretofore recognized or chracterized and no concentrate of isolation $^{125}$I-CEA-S$_1$ has been prepared. $^{125}$I-CEA-S$_1$ has been found consistently to have a buoyant density of about 1.41 ± 0.2 gm/ml in cesium chloride as distinguished in comparative measurements with $^{125}$I-CEA which demonstrated a wide range of density distribution having a major peak at about 1.36 gm/ml.

It is not possible to determine an absolute value for the molecular weight of either $^{125}$I-CEA or $^{125}$I-CEA-S$_1$ but comparative measurements of $^{125}$I-CEA and $^{125}$I-CEA-S$_{1\,S}$ using the same procedure and instrumentation and the same basic assumptions form a valid basis for distinguishing $^{125}$I-CEA-S$_1$ $_S$ from $^{125}$I-CEA. Using the Svedverg equation and the premises set forth hereinbefore, and comparative measurements, $^{125}$I-CEA-S$_1$ can be stated to be a distinct species of $^{125}$I-CEA having a molecular weight about 10 percent lower than the molecular weight of $^{125}$I-CEA; i.e., 181,000 daltons for $^{125}$I-CEA-S$_1$ as distinguished from 201,000 daltons $^{125}$I-CEA.

The relative mobility, Rm, of $^{125}$I-CEA-S$_2$ is distinct from that of $^{125}$I-CEA in comparative measurements. Using the standard acrylamide gel electrophoresis in 1% sodium dodecyl sulfate at pH7.0 (Weber et al, J. Biol. Chem. 244 : 4400–4412, 1969) and bromphenol blue as a marker to calculate relative mobility (Rm) in comparative tests, $^{125}$I-CEA-S$_1$ is distinct in that it demonstrates a single, discrete band of about 4% lower mobility, Rm = 0.143, than the wide diffuse band demonstrated by $^{125}$I-CEA.

As demonstrated, $^{125}$I-CEA-S$_1$ is strikingly, and unexpectedly, distinct immunochemically from $^{125}$I-CEA, although it is inherently more difficult to quantify immunochemical differences than physiciochemical differences. Immunochemically $^{125}$I-CEA-S$_1$ is distinct from $^{125}$I-CEA in a number of ways, the following distinguishing features being selected as being somewhat more subject to relative quantification or definition than other features.

A comparison of antigen binding characteristics provides one point distinguishing identification of $^{125}$I-CEA-S$_2$ as compared with $^{125}$I-CEA. While absolute values vary from sample to sample of CEA, the antigen binding capacity (ABC) of most anti-CEA antisera for $^{125}$I-CEA is significantly greater, generally by about 20 percent more, than that for CEA. Antigen binding capacities of about 10% or greater for $^{125}$I-CEA-S$_1$ than for $^{125}$I-CEA are significant and antigen binding capacities for $^{125}$I-CEA-S$_1$ range typically from about 15% to about %0% greater than for $^{125}$I-CEA in comparative tests.

The slope of the percent bound antigen ratio vs. antiserum concentration yielding linear regression slopes for the various samples of $^{125}$I-CEA-and for $^{125}$I-CEA-S$_1$ also provides an important distinguishing characteristic of $^{125}$I-CEA-S$_1$. The slope of the competitive inhibition curve for $^{125}$I-CEA-S$_1$ is substantially less vertical than the comparable curve for $^{125}$I-CEA, and typically the slope of the $^{125}$I-CEA-S$_1$curve is about three-fifths the slope of the $^{125}$I-CEA ABC assay. In general , the slope of the $^{125}$I-CEA curve will be from about one-half to about four-fifths the slope of the $^{125}$I-CEA curve in comparable tests, with some variability between antisera.

In another aspect of the invention, it has been discovered that by using a high ionic strength buffer, i.e., higher than physiologic, as the immunochemical reaction medium, the specificity of the diagnostic test is, contrary to prior description, very significantly improved thus eliminating high false-positive test results which may otherwise be experienced due to immunological cross reactions. A sodium chloride-borate buffer is used in the preceding examples but any fo the standard buffer systems at from about pH 7.5 to about 8.5 to 818 of higher than physiologic ionic strength may be used.

It is clearly understood that the invention contemplates one compositions, isolated $^{125}$I-CEA-S$_1$ (including its various forms such as radiolabelled, fluorescein or enzyme labelled $^{125}$CEA-S$_1$) and that while great effort and care has been exercised in specifying the various distinguishing physicochemical and immunochemical characteristics, the invention is not a particular characteristic or a particular set characteristic -- the invention is $^{125}$I-CEA-S$_1$, its method of isolation and concentration and its use. Consequently, while in the following claims the invention is defined in terms of physicochemical and immunochemical characteristics and related procedural steps, the substance of the invention is whether or not one has prepared or used labelled CEA-S$_1$ or a reagent prepared from CEA-S$_1$ such as antiserum or purified antibodies and not whether a particular characteristic is precisely accurate or whether a composition appears to exhibit some variation in some characteristic or set of characteristics by reason of differing techniques, skills, equipment, instruments or the like. Accordingly, recognizing limitations of the language, a full comprehension of the claimed invention requires recognition of the substance of the invention as hereinbefore stated and described.

BACKGROUND REFERENCES

Bjorklund, K.B. U.S. Pat. No. 3,823,126, July 9, 1974.

Burton, P., Chavanel, G., and Hirsch-Marie, H., Characterization of a second normal antigen that cross-reacts with CEA, J. Immunol., 111, 1926-1928 (1973).

Chisari, F. V., Gerin, J. L., and Edgington, T. S., Immunochemistry of the hepatitis B virus. $^{125}$I HB Agligand. J. Immunol., 113, 543–553 (1974).

Coligan, J. E., Lautenschleger, J. T., Egan, M. L., and Todd, C. W. Isolation and characterization of carcinoembryonic antigen. Immunolchemistry 9,377–387 (1972).

Coligan, J. E., Henkart, P. A., Todd, C. W., and Terry, W. D.,

Heterogeneity of the carcinoembryonic antigen, Immunolchemistry 10, 591–599 (1973). Cuatrecases, P., Wilchak, M., and Anfinsen, C. B., Selective enzyme purification by affinity chromatography. Biochemistry, 61, 636–643 (1968).

Edgington, T. S., CEA-S: A distinctive isomeric variant of carcinoembryonic antigen. Fed. Proc., 34, 845 (1975).

Edgington, T. S., and Plow, E. F., Conformational and structural modulation of the N-terminal regions of fibrinogen and fibrin associated with plasmin cleavage. J. Biol. Chem., in press (1975).

Eveleigh, J. W. Heterogeneity of carcinoembryonic antigen. Cancer Res., 34, 2122–2124 (1974).

Freedman, S. O., Gold, P., Krupey, J. H., U.S. Pat. No. 3,663,684, May 16, 1972.

Gelotte, B. J., Studies on gel filtration. Sorption properties of the bed material sephadex. J. Chromatog., 3, 330–342 (1960).

Gold, J. M., Banjo, C., Freedman S. O., et al: Immunochemical studies of the intramolecular heterogeneity of the carcinoembryonic antigen (CEA) of the human digestive system. J. Immunol 111:1872–1879, 1973.

Gold, P., and Freedman, S. O., Specific carcinoembryonic antigens of the human digestive system. J. exp. Med., 122, 467–481 (1965).

Gold, P., Freedman S. O.: Demonstration of tumor-specific antigens in human colomic carcinomata by immunological tolerance and absorption techniques. J. Exp. Med., 121:439–462, 1965.

Gold, P., Gold M., Freedman S.O.; : Cellular localization of carcinoembryonic antigens of the human digestive system. Cancer Res. 28:1331-1334, 1968.

Gold, J. M., and Gold, P., The blood group A-like site on the carcinoembryonic antigen. Cancer Res., 33, 2821–2824 (1973).

Goldenberg, D. M., U.S. Pat. No. 3,865,689, Feb. 11, 1975. Hansen, H. J., Carcinoembryonic antigen (CEA) assay, A laboratory adjunct of the diagnosis ad management of cancer. Hum. Path., 5, 139-147 (1974).

Hansen, H. J., U.S. Pat. Nos. 3,697,638, Oct. 10, 1972, and 3,867,363, Feb. 18, 1975.

Krupey, J., Gold, P., and Freedman, S., Physicochemical studies of the carcinoembryonic antigens of the human digestive system. J. exp. Med., 128, 387–398 (1968). Linder, E. J., and Edgington, T. S., Ultramicro assay of anti-erythrocyte antibodies and erythrocyte antigens. Vox Sang., 21, 222–232 (1971).

Lo Gerfo, P., Krupey. J., and Hansen, H. J., Demonstration of an antigen common to several varieties of neoplasia. New Engl. J. Med., 285, 138–141 (1971).

Mach, J. P., and Pusztaszeri, G., Carcinoembryonic antigen (CEA); Demonstration of a partial identity between CEA and a normal glycoprotein. Immunochemistry, 9. 1031-1034 (1972).

Moore, T. L., Kupchik, H. Z., Marcon, N., and Zamcheck, N., Carcinoembryonic antigen assay in cancer of the colon and pancreas and other digestive tract disorders. Amer. J. dig. Dis., 16, 1–7 (1971).

Newman, E. S., Petras, S. E., Georgiadis, A., and Hansen, H. J., Interrelationship of carcinoembryonic antigen and colon carcinoma antigen III, Cancer Res., 34, 2125–2130 (1974).

Ornstein, L., Disc electrophoresis. Ann. N.Y. Acad. Sci., 121, 321–349 (1964).

Plow, E., and Edgington, T. S., Molecular events responsible for modulation of neoantigenic expression: The cleavage-associated neoantigen of fibrinogen. Proc. nat. Acad. Sci. (Wash.) 69, 208–212 (1972).

Plow, E. F. and Edgington, T. S., Immunobiology of fibrinogen. Emergence of neoantigenic expressions during physiologic cleavage in vitro and in vivo. J. Clin. Invest., 52, 273–282 (1973a).

Plow, E. F., and Edgington, T. S., Discriminating neoantigenic differences between fibrinogen and fibrin derivatives. Proc. nat. Acd. Sci. (Wash.), 70, 1169–1173 (1973b).

Plow, E. F., Edgington, T. S.: Isolation and characterization of a homogeneous isomeric species of carcinoembryonic antigen: CEA-S. Int. J. Cancer 15:748–761, 1975.

Pusztaszeri, G., and Mach, J. P., Carcinoembryonic antigen (CEA) in non-digestive cancerous and normal tissues. Immunochemistry 10, 197–204 (1973).

Rule, A. H., and Goleski-Reilly, C., Phasespecific oncocolon antigens: A theoretical framework for carcinoembryonic antigen specificities. Cancer Res., 34, 2083–2087 (1974).

Siegel, L. M., and Monty, K. J., Determination of molecular weights and frictional ratios of proteins in impure systems by use of gel filtration and density gradient centrifugation. Application to crude preparations of sulfite and hydroxylamine reductases. Biochem. Biophys. Acta., 112, 346–362 (1966).

Simmons, A. R., and Perlman, P., Carcinoembryonic antigen and blood group substances. Cancer Res., 33, 313–322 (1973).

Terry, W. D., Henkart, P., Coligan, J. E., and Todd, C. W., Carcinoembryonic antigen: Characterization and clinical applications. Transplant. Rev., 20, 100–129 (1974).

Terry, W. D., Henkart, P., Coligan, J. E., and Todd, C. W., Structural studies of the major glycoprotein preparations with carcinoembryonic antigen activity. J. exp. Med., 136, 200–204, (1972).

Thompson, D. M. P., Krupey, J., Freedman, S. O., and Gold, P., The radioimmunoassay of circulating carcinoembryonic antigen of the human digestive system. Proc. nat. Acad. Sci. (Wash.), 64, 161–167 (1969).

Turner, M. D., Olivares, T. A., Harwell, L., and Kleinman, M. S., Further purification of perchlorate-soluble antigens from human colonic carcinomata. J. Immunol., 180, 1328–1339 (1972).

Von Kleist, S., Chavanel, G., and Burtin, P., Identification of an antigen from normal human tissue that crossreacts with the carcinoembryonic antigen. Proc. nat. Acad. Sci. (Wash.), 69, 2492–2494 (1972).

Weber, K., and Osborn, M., The reliability of molecular weight determinations by dodecyl sulfate-polyacrylamide. gel electrophoesis. J. Biol. Chem., 244, 4406–4412 (1969).

Winzor, D. J., Analytical gel filtration. In:S. J. Leach (ed.), Physical principles and techniques of protein chemistry, part A, pp. 451–494, Academic Press, New York (1969).

We claim:

1. A radioimmunoassay reagent consisting essentially of the radiolabelled, isolated species of carcinoembryonic antigen denominated CEA-$S_1$, said species being characterized by such physicochemical and immunochemical characteristics as:
   (a) having a single, discrete isoelectric point of about 4.5, as measured by isoelectric columns with ampholytes having a pH range of 3 to 6 or by thin layer pH 3 to 9 acrylamide gels containing ampholytes;
   (b) having a buoyant density of about 1.41, as measured by isopyknic equilibrium density gradient ultracentrifugation in cesium chloride solution;
   (c) having a molecular weight of about 181,000 daltons as calculated from the Svedberg equation;
   (d) precipitating with anti-carcinoembryonic antigen, precipitating preferentially with anti-CEA-$S_1$, but not precipitating with antisera to blood group A or B or antisera to normal tissue glycoprotein;
   (e) having a percent bound antigen vs. antiserum concentration linear regression slope of from about one half to about four fifths the slope of a like curve for carcinoembryonic antigen comparatively tested against identical anti-carcinoembryonic antigen in high ionic strength buffer.

2. The radioimmunoassay reagent consisting essentially of the radiolabelled, isolated tumor-associated antigen denominated CEA-$S_1$ suitable for use as an aid in the diagnosis of cancer of the human gastrointestinal tract, consisting essentially of the isomer of carcinoembryonic antigen isolated and concentrated from glycoprotein extract of human adenocarcinomas of the intestinal tract being characterized by such physicochemical and immunochemical characteristics as:

having a sedimentation velocity of $S°_{20,w}$ = about 6.6 Svedberg units when analyzed by linear sucrose density ultracentrifugation as distinguished from carcinoembryonic antigen having a sedimentation velocity of about 6.8 as determined by the same method;

precipitating with antiserum to carcinoembryonic antigen and antiserum to carcinoembryonic antigen isomer in gel double diffusion to give an arc of apparent identity with carcinoembryonic antigen, being preferentially bound by antiserum carcinoembryonic antigen isomer, but not being bound by antisera to blood group A or B or antisera to normal tissue glycoprotein;

having a single discrete isoelectric point of about 4.5 measured by isoelectric columns with ampholytes having a pH range of 3 to 6 or by thin layer pH 3 to 9 acrylamide gels containing ampholytes as distinguished from carcinoembryonic antigen isomer which exhibits a distribution of isoelectric points over the range of from about 3 to about 5.2;

being indistinguishable from carcinoembryonic antigen when characterized by Sephadex G-200 gel exclusion chromatography;

having a buoyant density when isolated from typical colonic adenocarcinomas of about 1.41 when measured by isopyknic equilibrium density gradient ultracentrifugation in cesium chloride solution; and an estimated molecular weight of about 181,000 daltons as calculated from the Svedberg equation
$$M = sRT/D(1 - \bar{v}\rho)$$

wherein s is the sedimentation coefficient measured by linear sucrose density ultracentrifugation, D is the diffusion constant as measured by molecular exclusion chromatography on Sephadex G-200 equilibrated with 0.14 M. NaCl, 0.01 sodium phosphate at pH 6.0, $\bar{v}$ is the partial specific volume estimated as the reciprocal of buoyant density by isopyknic density gradient ultracentrifugation in CsCl, $\rho$ is the density of solution for sedimentation coefficient analysis corrected to 1.00, R is the gas constant and T is the absolute temperature, as distinguished from carcinoembryonic antigen having an estimated molecular weight of about 201,000 measured in the same manner.

3. The radioimmunoassay reagent consisting essentially of a radiolabelled isolated species of carcinoembryonic antigen denominated CEA-$S_1$ characterized by:
having an antigen binding capacity of anti-CEA for CEA-$S_1$ significantly greater by at least about 10 percent than the antigen binding capacity for CEA for the same anti-CEA in comparative tests; and
having a percent bound antigen vs. antiserum concentration linear regression slope substantially less, from about one half to about four fifths the slope of a like curve for CEA comparatively tested against identical anti-CEA in high ionic strength buffer.

4. The method of preparing a radioimmunoassay reagent of an isolated species of carcinoembryonic antigen denominated CEA-$S_1$, comprising the steps of:
   (a) extracting from adenocarcinomas of the human gastrointestinal tract glycoproteins including carcinoembryonic antigen;
   (b) isolating from said glycoproteins the carcinoembryonic antigen;
   (c) isolating from the carcinoembryonic antigen that species which is characterized by having an antigen binding capacity of anti-CEA for CEA-$S_1$ significantly greater by at least about 10 percent than the antigen binding capacity for CEA for the same anti-CEA in comparative tests, and by having a percent bound antigen vs. antiserum concentration linear regression slope substantially less, from about one half to about four fifths the slope of a like curve for CEA comparatively tested against identical anti-CEA in high ionic strength buffer; and (d) radiolabelling the resulting isolated CEA-S$_1$.

5. The method of preparing a immunoassay reagent of an isolated species of carcinoembryonic antigen denominated CEA-S$_1$, comprising the steps of:
   (a) extracting from adenocarcinomas of the human gastrointestinal tract glycoproteins including carcinoembryonic antigen;
   (b) isolating from said glycoproteins the carcinoembryonic antigen;
   (c) isolating from the carcinoembryonic antigen that species which is characterized by having an estimated molecular weight of about 181,000 daltons as calculated from the Svedberg equation M = SRT/D(1−$\bar{v}\rho$) wherein s is the sedimentation coefficient measured by linear sucrose density ultracentrifugation D is the diffusion constant as measured by molecular exclusion chromatography on Sephadex G-200 equilibrated with 0.14 M. NaCl, 0.01 sodium phosphate at pH 6.0, $\bar{v}$ is the partial specific volume estimated as the reciprocal of buoyant density by isopyknic density gradient ultracentrifugation in CsCl, $\rho$ is the density of solution for sedimentation coefficient analysis corrected to 1.00, R is the gas constant and T is the absolute temperature, as distinguished from carcinoembryonic antigen having an estimated molecular weight of about 201,000 measured in the same manner, a single discrete isoelectric point of about 4.5 plus or minus 0.1, a sedimentation velocity of about 6.6 Svedberg units and the immunochemical characteristic of precipitating with anti-carcinoembryonic antigen, precipitating preferentially with anti-carcinoembryonic antigen species, but not precipitating with antisera to blood group A or B or antisera to normal tissue glycoprotein, and
   (d) labelling the resulting CEA-S$_1$.

6. The method of preparing an immunoassay reagent of an isolated species of carcinoembryonic antigen denominated CEA-S$_1$, comprising the steps of:
   (a) extracting glycoprotein from adenocarcinomas of the human gastrointestinal tract;
   (b) isolating extracted glycoproteins having a PI of about 4.5 plus or minus 0.1 from the glycoproteins extracted in step (a);
   (c) isolating from the product of step (b) the glycoproteins having an average molecular weight of about 200,000 daltons as measured by molecular exclusion chromatography on Sephadex G-200 equilibrated with 0.14 M. NaCl, 0.01 sodium phosphate, pH 6.0;
   (d) fractionating by charge density relative to binding to the ion exchange resin DEAE - cellulose with recovery of the first major peak during elution in 0.05 M Na$_2$HPO$_4$, pH 8.
   (e) removing from the product of step (c) other proteins, glycoproteins and blood group antigens related molecules by immunoabsorption;
   (f) isolating from the product of step (d) the glycoprotein having a buoyant density of about 1.41 g/ml; and
   (g) labelling the resulting CEA-S$_1$.

7. The method of preparing an immunoassay reagent of an isolated species of carcinoembryonic antigen denominated CEA-S$_1$, comprising the steps of:
   (a) extracting glycoproteins from adenocarcinomas of the human gastrointestinal tract;
   (b) isolating by isoelectric focusing of extracted glycoproteins that glycoprotein fraction having an isoelectric point of about 4.5;
   (c) isolating by molecular exclusion chromatography that fraction of glycoprotein having an isoelectric point of about 4.5 and an average molecular weight of about 200,000 daltons as measured by molecular exclusion chromatography on Sephadex G-200 equilibrated with 0.14 M. NaCl, 0.01 sodium phosphate at pH 6.0;
   (d) fractionating by charge density relative to binding to the ion exchange resin DEAE - cellulose with recovery of the first major peak during elution in 0.05 M Na$_2$HPO$_4$, pH 8;
   (e) removing from the fraction of glycoprotein having an isoelectric point of about 4.5 and a molecular weight of about 200,000 daltons by immunoabsorption of proteins, glycoproteins other than carcinoembryonic antigen species, and blood group antigen related molecules;
   (f) isolating by isopyknic density gradient ultracentrifugation that fraction of glycoproteins which are carcinoembryonic antigen species having an estimated molecular weight of about 181,000 daltons as calculated from the Svedberg equation M = sRT/D(1−$\bar{v}\rho$) wherein s is the sedimentation coefficient measured by linear sucrose density ultracentrifugation, D is the diffusion constant as measured by molecular exclusion chromatography on Sephadex G-200 equilibrated with 0.14 M. NaCl, 0.01 sodium phosphate at pH 6.0, $\bar{v}$ is the partial specific volume estimated as the reciprocal of buoyant density by isopyknic density gradient ultracentrifugation in CsCl, $\rho$ is the density of solution for sedimentation coefficient analysis corrected to 1.00, R is the gas constant and T is the absolute temperature, as distinguished from carcinoembryonic antigen having an estimated molecular weight of about 201,000 measured in the same manner; and an isoelectric point of about 4.5 and being free of other glycoproteins and proteins and blood group antigen related moleculel and
   (g) labelling the resulting isolated CEA-S$_1$.

8. The product of the process of claim 7.

9. In the diagnosis of human gastrointestinal cancer, the improvement in the competitive inhibition immunoassay of carcinoembryonic antigen wherein the immunoassay reagent comprises a labelled isolated species of carcinoembryonic antigen denominated CEA-S$_1$ and wherein the antigen-antibody reaction is carried out in high ionic strength buffer, to thereby give specificity for antigens resulting from gastrointestinal cancer said labeled isolated species of carcinoembryonic antigen denominated CEA-S$_1$ characterized by having an antigen binding capacity of anti-CEA for CEA-S$_1$ significantly greater by at least about 10 percent.

10. The improved method of Claim 9 wherein the buffer consists essentially of an aqueous solution of sodium chloride and sodium borate at about pH 7.5 to pH 8.8.

11. In the radioimmunoassay for CEA, the improved method wherein the radioimmunoassay reagent is a radiolabelled, isolated species of carcinoembryonic antigen denominated CEA-S$_1$.

12. In the radioimmunoassay of CEA, the improved method wherein the radioimmunoassay reagent consists essentially of a species of carcinoembryonic antigen denominated $^{125}$I-CEA-S$_1$ characterized by having an antigen binding capacity of anti-CEA for CEA-S$_1$ significantly greater by at least 10 percent.

13. The improved competitive inhibition radioimmunoassay method for aiding in the diagnosis of cancer in the gastrointestinal tract of man comprising the use of a radiolabelled isolated species of carcinoembryonic antigen denominated CEA-S$_1$ as the radioimmunoassay reagent said reagent being characterized by having an antigen binding capacity of anti-CEA for CEA-S$_1$ significantly greater by at least 10 percent.

* * * * *